US00PP35910P2

(12) United States Plant Patent
Rosas et al.

(10) Patent No.: US PP35,910 P2
(45) Date of Patent: Jul. 2, 2024

(54) STRAWBERRY PLANT NAMED 'PLARED 19011'

(50) Latin Name: ***Fragaria* x *ananassa***
Varietal Denomination: Plared 19011

(71) Applicant: Plantas de Navarra S.A., Valtierra (ES)

(72) Inventors: Manuel Rosas, Anderson, CA (US); Craig Gaines, Anderson, CA (US)

(73) Assignee: Plantas de Navarra S.A., Valtierra (ES)

( * ) Notice: Subject to any disclaimer, the term of this patent is extended or adjusted under 35 U.S.C. 154(b) by 0 days.

(21) Appl. No.: 18/445,241

(22) Filed: Jun. 13, 2023

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./209
CPC ..... A01H 5/08; A01H 5/00; A01H 6/7409; A01H 6/74
See application file for complete search history.

(56) References Cited

U.S. PATENT DOCUMENTS

PP20,552 P3 12/2009 Shaw et al.

*Primary Examiner* — June Hwu
(74) *Attorney, Agent, or Firm* — Hunt IP Law

(57) ABSTRACT

The new and distinct variety of strawberry plant variety 'Plared 19011' is provided. The variety can be distinguished by its outstanding features of an upright plant architecture, darker red and firmer long conical fruit, and greater yield from summer planting.

3 Drawing Sheets

Latin name of the genus and species:
Botanical classification:
a. Genus—*Fragaria.*
b. Species—x *ananassa.*
Variety denomination: The new strawberry plant claimed is of the variety denominated 'Plared 19011'.

BACKGROUND OF THE INVENTION

Field of the Invention

The present invention relates to a new and distinct annual variety of strawberry plant, which has been given the variety denomination of 'Plared 19011'.

Background of the Related Art

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberries are an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

The present invention relates to a new and distinct annual variety of strawberry, which has been given the variety denomination of 'Plared 19011'. Its market class is that of summer planted variety. 'Plared 19011' is intended for use as a frigo plant to be planted in the summer and produce fresh fruit in the fall and beyond.

The new strawberry variety is a selection resulting from a sexual cross of strawberry plants at Watsonville, California in 2019, involving a seed parent known as '16-069R' (unpatented) and a pollen parent known as '15-263R' (unpatented).

The selection was subsequently evaluated for four years in Watsonville, California.

Asexual reproduction of the new variety by cutting propagation since 2019 Watsonville, California has demonstrated that the new variety reproduces true to type with all of the morphological characteristics, as herein described, firmly fixed and retained through successive generations of such asexual propagation.

Selection criteria was based on the needs the California fresh fruit market and was optimized for the summer planting for targeted production ideotype.

Plants of the new variety differ from plants of the seed parent '16-069R' as the plant architecture is more upright, the fruit are long conical instead of short conical, and the marketable yield in summer planting is greater. Plants of the new variety differ from plants of the pollen parent '15-263R' in that the plants are adapted for summer planting using frigo plants and produce a fruit which is both darker tint of red and firmer than those of '15-263R'. 'Plared 19011' presents as brick red fruit (sRGB 192, 51, 38) in contrast with '15-263R' that presents as light red (sRGB 228, 0, 43). Main differences between 'Plared 19011' and known variety 'Portola':

a. Density of foliage: medium for 'Plared 19011' and strong for 'Portola'
b. Vigor: medium for 'Plared 19011' and strong for 'Portola'
c. Fruit color: brick red for 'Plared 19011' and light red for 'Portola'.

BRIEF DESCRIPTION OF THE DRAWINGS

The accompanying photographic illustrations show the typical appearance of the new variety 'Plared 19011'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

Figure 1:
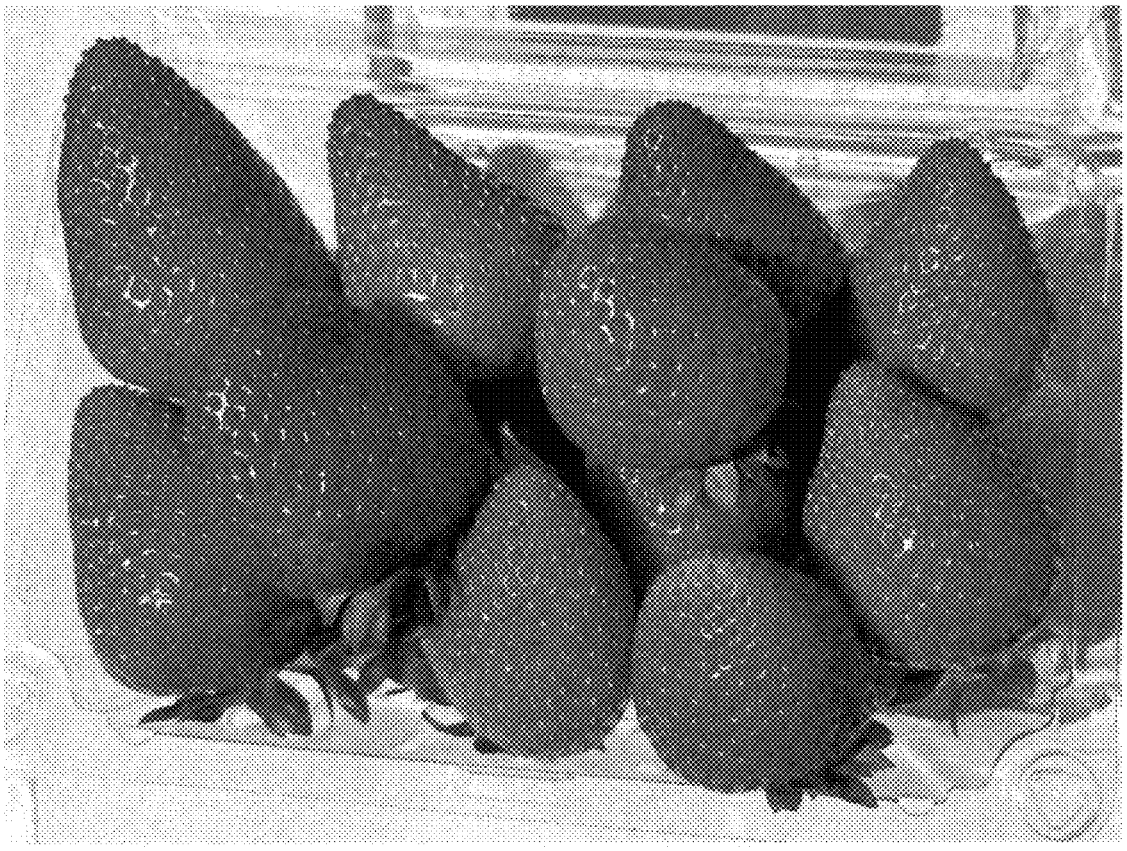
FIG. 1 is a photograph of the new variety 'Plared 19011', demonstrating its dark red conical elongated fruit.
Figure 2:
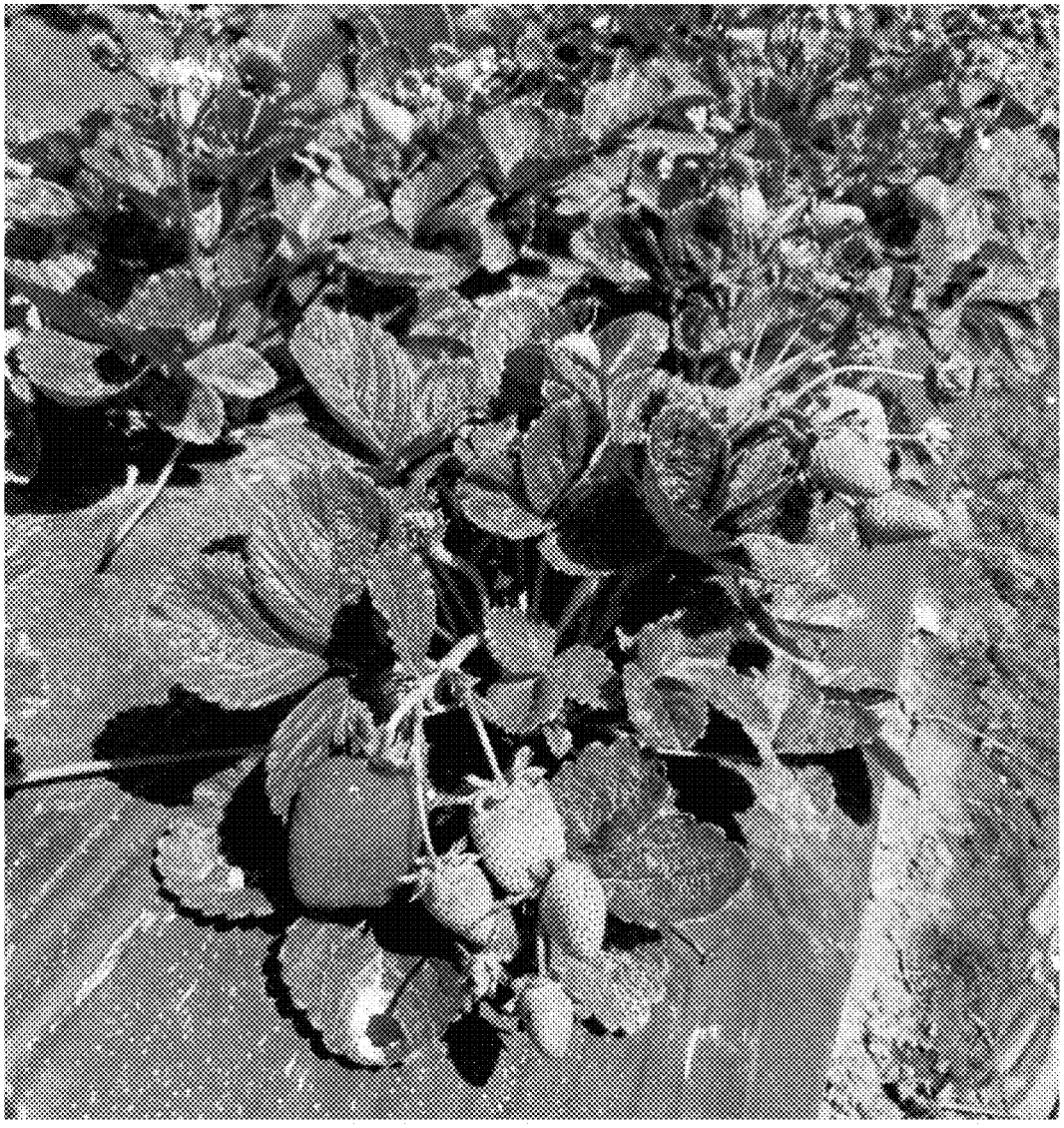
FIG. 2 is a photograph of the upright architecture and summer planting adaptation of the new variety 'Plared 19011'. This photo was taken on Aug. 24, 2022, 73 days after planting using frigo plants.
Figure 3:
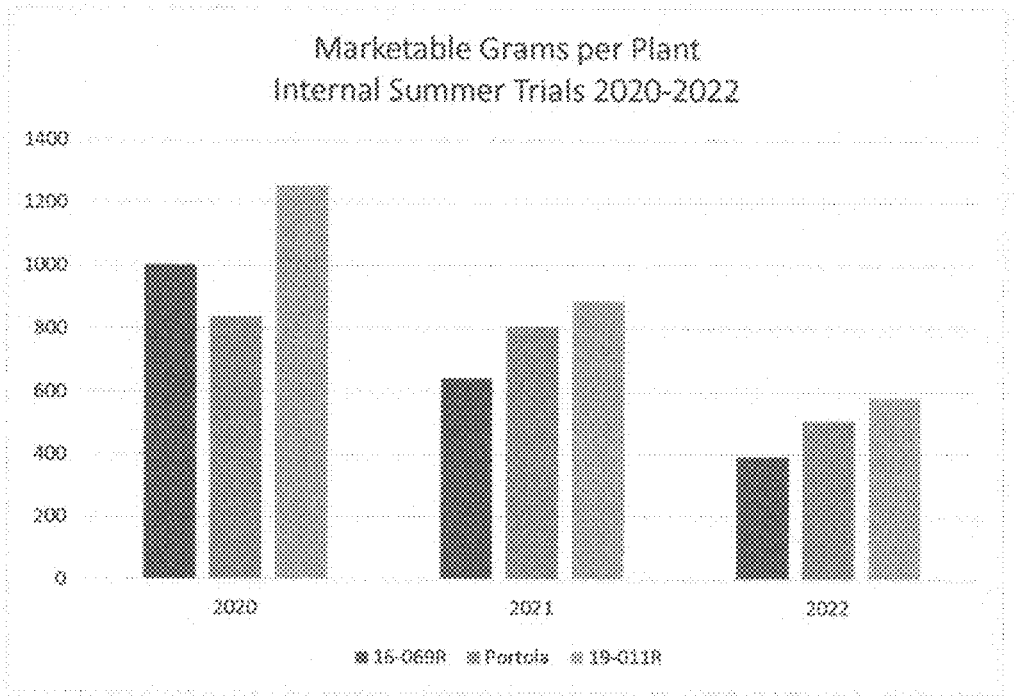
FIG. 3 is a bar graph of marketable yield over three summer planting seasons of new variety 'Plared 19011', seed parent 16-069R, and industry reference 'Portola' (U.S. Plant Pat. No. 20,552).

The following detailed description sets forth the distinctive characteristics of 'Plared 19011'. The datum which defines these characteristics was collected from asexual reproductions of the original selection. Dimensions, sizes, colors, and other characteristics are approximations and averages set forth as accurately as possible. The plant history was taken on plants approximately 135 Days, and the descriptions relate to plants grown in Watsonville, California. Color notations are in reference to the standard RGB (sRGB) color space.

Classification:

a. *Family.*—Rosaceae.
b. *Botanical.*—*Fragaria.*
c. *Common name.*—Strawberry.
d. *Variety name.*—'Plared 19011'.

Parentage:

a. *Female parent.*—'16-069R'.
b. *Male parent.*—'15-263R'.

PLANT

General:

a. *Height.*—20 cm.
b. *Diameter.*—25.5 cm.
c. *Number of crowns per plant.*—4.
d. *Growth habit.*—Upright.
e. *Density of foliage.*—Medium to High Density.
f. *Vigor.*—Medium.
g. *Stolon.*—i. Average number of daughter plants per sq. ft. — 8.2. ii. Diameter at bract — 0.95 cm. iii. Anthocyanin coloration — Medium. iv. Anthocyanin color — Light Red. v. Stolon color — Light Green (sRGB 111, 137, 35). vi. Density of pubescence on the stolon — Medium.
h. *Hardiness zone.*—16° C.-27° C., hardiness zone 13.

LEAVES

General:

a. *Number of leaflets.*—3.
b. *Color of upper surface.*—Dark Green (sRGB 41, 75, 0).
c. *Color of lower surface.*—Light Green (sRGB 106, 127, 79).
d. *Leaf blistering.*—Medium to Strong.
e. *Leaf glossiness.*—Medium to Strong.
f. *Variegation.*—Absent.
g. *Terminal leaflet.*—i. Length — 7.6 cm. ii. Width — 7.6 cm. iii. Length/width ratio — 1. iv. Number of teeth/terminal leaflet — 22. v. Shape of base — Rounded. vi. Margin — Crenate. vii. Shape in cross section — Concave to Straight. viii. Shape of apex — Rounded.
a. *Petiole.*—i. Length — 11.5 cm. ii. Diameter — 0.65 cm. iii. Attitude of hairs — Outward. iv. Bract frequency (number present on each petiole) — N/A. v. Color — Light Green (sRGB 103, 120, 67).
b. *Petiolule.*—i. Length — 5-7 mm. ii. Color — Light Green (sRGB 103, 120, 67).
c. *Stipule.*—i. Length — 2.2 cm. ii. Width — 1.25 cm. i. Anthocyanin coloration — Present. ix. Anthocyanin color — Pink (sRGB 255, 102, 178). x. Stipule color — Light Green with Light Red Accents (sRGB 166, 149, 109).

INFLORESCENCE

General:

a. *Position in relation to foliage.*—Above.
b. *Pedicel.*—i. Attitude of hairs — Outward. ii. Length — 14 cm. iii. Diameter — 0.5 cm. iv. Color — Light Green (sRGB 103, 120, 67).
c. *Flower.*—i. Arrangement of petals — Overlapping. ii. Stamen — Present. iii. Anther color (if stamen is present) — Dark Yellow (sRGB 205, 169, 95). iv. Number of flowers per inflorescence — 2-6. v. Mean diameter of individual flower — 31.2 mm.
d. *Petal.*—i. Length/width ratio — Equal. ii. Typical and observed petal number — White. iii. Color of upper side — White (sRGB 255, 255, 255). iv. Color of lower side — White (sRGB 255, 255, 255).
e. *Calyx.*—i. Color — Green (sRGB 0, 51, 0). ii. Mean diameter — 28 mm.

f. *Sepal*.—i. Color of upper surface — Green (sRGB 0, 51, 0). ii. Color of lower surface — Light Green (sRGB 94, 99, 56). iii. Attitude of sepals — Outward to away from berry.

FRUIT

General:

a. *Fruit weight*.—29 grams (2022 season average).
b. *Shape*.—Conical.
c. *Differences in shape between primary and secondary fruit*.—Moderate.
d. *Glossiness*.—Medium.
e. *Firmness*.—Strong Firmness.
f. *Color*.—Brick Red (sRGB 192, 51, 38).
g. *Evenness of fruit color*.—Even.
h. *Position of achenes*.—Level with Surface.
i. *Number of fruit per truss*.—4.
j. *Position of calyx attachment*.—Inserted.
k. *Color of flesh* (*excluding core*).—Red (sRGB 133, 74, 67).
l. *Color of core*.—Red with White (sRGB 133, 74, 67).
m. *Sugar content* (*as soluble solids in degrees brix*).—9.9% (2022 season average).
n. *Production*.—i. Flowering interval — Beginning approximately 2 weeks of planting in summer with frigo plants, continuous flowering thereafter. ii. Harvest interval — Beginning approximately 6 weeks after planting in summer with frigo plants, continuous harvest thereafter. iii. Type of bearing — Day-Neutral. iv. Productivity — Three-year average of 908 grams per plant produced within five months of summer planting using frigo plants (e.g., planting in early June and harvesting through October).
o. *Resistance/susceptibility to pathogens*.—i. *Fusarium oxysporum* — Resistant.
p. *Width of band without achenes*.—Absent or very narrow.
q. *Adherence to calyx*.—Strong.
r. *Cavity size*.—Absent or small.
s. *Fruit length*.—52 mm average (range: 48-56 mm).
t. *Fruit diameter*.—40 mm average (range: 38-42 mm).
u. *Storage life*.—Very good storage life; average shelf life of 7 days at a temperature of 4.5° C.
v. *Market use*.—Commercial fresh fruit market.

What is claimed is:

1. A new and distinct variety of strawberry plant named '19011', as illustrated and described herein.

* * * * *